United States Patent [19]

Matsumoto et al.

[11] Patent Number: 4,792,638
[45] Date of Patent: Dec. 20, 1988

[54] ISOLATION PROCESS OF 2-CHLOROETHYL VINYL ETHER

[75] Inventors: Tsuyoshi Matsumoto; Toshiyuki Fukudome; Masaaki Tsuchida, all of Ichihara, Japan

[73] Assignee: Nisso Maruzen Chemical Co., Ltd., Tokyo, Japan

[21] Appl. No.: 173,737

[22] Filed: Mar. 23, 1988

[30] Foreign Application Priority Data

Apr. 3, 1987 [JP] Japan .................. 62-82600

[51] Int. Cl.$^4$ ................ C07C 41/34; C07C 41/28
[52] U.S. Cl. ................................ 568/682; 568/686
[58] Field of Search ........................ 568/682, 686

[56] References Cited

U.S. PATENT DOCUMENTS 3,023,250  2/1962  Montagna et al. .............. 568/686
4,396,782  8/1983  Eldin ................................ 568/686

Primary Examiner—Howard T. Mars
Attorney, Agent, or Firm—George B. Oujevolk

[57] ABSTRACT

The present invention relates to an isolation process of 2-chloroethylvinyl ether from a thermal decomposition product of 1,1-di(2-chloroethoxy)ethane, and comprises the azeotropic distillation of 2-chloroethyl vinyl ether and 2-chloroethanol from the product, the reaction of the 2-chloroethanol in the azeptrope with the 2-chloroethyl vinyl ether to 1-1-di(2-chloroethoxy)ethane without the separation from the product, and the purification of 2-chloroethyl vinyl ether by the rectification of the above reaction mixture.

1 Claim, No Drawings

ISOLATION PROCESS OF 2-CHLOROETHYL VINYL ETHER

BACKGROUND OF THE INVENTION (1) Field of the Invention

The present invention relates to an isolation process of 2-chloroethyl vinyl ether which is useful for the raw material of various functional polymers.

(2) Description of the Prior Art

U.S. Pat. No. 3,023,250 discloses the process in which 1,1-di(2-chloroethoxy)ethane (hereinafter, called as CEE.) is decomposed thermally in the presence of an acidic catalyst, followed immediately by the conversion to an alkalinic reaction condition, and resulting in production of 2-chloroethyl vinyl ether (hereinafter, called as CEVE.).

In the above patent, CEE is decomposed in the presence of an acidic catalyst according to the formula shown below,

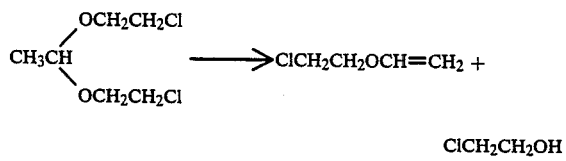

$$ClCH_2CH_2OH$$

to CEVE and 2-chloroethanol (hereinafter, called as CE.) but, if the decomposition is continued under an acidic circumstance due to the hydrogen chloride in the decomposition gas or an acid catalyst, the reverse reaction in which CEVE with CE returns to CEE or the polymerization reaction of CEVE itself proceeds dominantly. As a result, CEVE can be scarcely produced. Further, the patent suggests that such a base as an amine shall be employed immediately in the decomposition mixture to avoid the phenomenon. Namely, both the decomposition reaction and the recombination reaction are suggested to proceed at the same time at an elevated temperature in this reaction system.

As is shown in the above reaction scheme, the product, CEVE, the unreacted CEE and an equivalent mol. of the by-produced CE to CEVE exist in the decomposition mixture. But, the complete separation of CEVE from CE by a few distillations is actually impossible because CEVE distills azeotropically with CE. So, the above U.S. patent proposes that the azeotrope shall be washed with water, water-soluble CE shall be transferred to the water layer and the crude CEVE shall be dried and purified by distillation.

However, much water in the washing shall be dumped as waste water, and, further, because of the extreme difficulty in the recovery of CE mingled in the water layer, an uneconomic desertation of the CE occurs. These are serious disadvantages in the prior art.

If the CE existing in the aforementioned azeotrope can be changed to a raw material relating to the present process without the separation from the azeotrope, all of the by-produced CE can be utilized in a skillful manner.

SUMMARY OF THE INVENTION

In consideration of all the aforementioned problems, the inventors examined various methods of utilizing the CE effectively without dumping the CE in the azeotrope into the washing water, and easy methods of isolating CEVE having a high purity. As a result, the inventors discovered that only the aforementioned recombination reaction proceeds even in an acidic condition, even if the temperature is below a specified level.

Namely the present invention relates to an isolation process of CEVE having a high purity from the thermal decomposition mixture of CEE, which comprises the following procedures;

(1) separating the fraction consisting of mainly CEVE and partially of CE from the said thermal decomposition mixture;

(2) acidifying the said fraction, then without separating the above two compounds, reacting the said CE with a part of CEVE at a temperature below 100° C. to CEE, and making the said fraction consist of CEVE and CEE;

(3) isolating CEVE from CEE by rectification.

DESCRIPTION OF PREFERRED EMBODIMENTS

Any decomposition mixture produced under various conditions of the reaction illustrated above can be used in the present process, and some examples of the reaction conditions are disclosed in the aforementioned U.S. patent or Japanese unexamined patent application No. 57-139030. According to their process out-lines, CEE is decomposed in the presence of an acid or calcium oxide in the temperature range from 100° C. to 200° C.

In the present process:

(a) At first, the azeotrope consisting of most part of CEVE and a little part of CE is separated from the residue consisting of most part of CE and the unreacted CEE by a simple distillation of the above decomposition mixture.

As the recombination reaction reverse to the decomposition reaction occurs also if the distillation circumstance is acidic and the temperature is elevated, CEVE reacts with CE to CEE. Further, in the same manner, the polymerization reaction of CEVE itself may easily occur, and, thereby, the decomposition mixture shall be neutral or basic by the employment of a base prior to the distillation.

The CE in the residue can be reacted, for example, with acetaldehyde, without separating from the residue, then the residue essencially consists of CEE, which can be recycled as the raw material of the decompo-sition reaction.

(b) Next, the CE shall be separated from the CEVE in the basic azeotrope, but it can not be separated by distillation. According to the novel fact that the CE can react with CEVE and can be turned back to CEE even if the azeotrope is acidic and the temperature is kept at below 100° C., the CE is turned back to CEE without separating from the azeotrope after the azeotrope has been acidified.

Of course, an equi-mol of CEVE to that of CE is spent in this step, and the yield decreases a little after the rectification mentioned in step (c), which shall never be a serious problem in consideration of the simple operations and the high purity of CEVE produced in the present process.

As an acid used in this step, hydrogen chloride, sulfuric acid, phosphoric acid, p-toluene sulfonic acid or so is exemplified, the quantity of the acid added to the basic azeotrope depends on its basisity, and 0.01 to 1.0 weight % of the acid to the azeotrope shall be added in addition to the amount necessary for the neutralization of the azeotrope.

After the operation in step (b), only two compounds, CEVE and CEE, exist in the subject mixture and the aforementioned azeotropic distillate consisting of CEVE and CE shall not be obtained at all by distillation. Then the mixture is heated and is rectified by a well-known distillation method. And a highly purified CEVE can be obtained as a distillate. Further, most part of the residual mixture stayed in the distillation still consists of CEE, which can be recycled, as it is or after washing if necessary, to the aforementioned decomposition reaction.

Further, the rectification shall be carried out at a temperature as low as possible to avoid the thermal polymerization of CEVE itself. Accordingly, the distillation temperature is preferablly kept in the range from 50° C. to 100° C.

As is mentioned above, though CEVE could be synthesized skilfully in the process of U.S. Pat. No. 3,023,250, the isolation of a highly purified CEVE was difficult. On the other hand, a highly purified CEVE containing little water can be obtained in good yield according to the present process.

For the purpose of giving those skilled in the art a better understanding of the present process, the following reference examples, examples and a comparison example are given.

REFERENCE EXAMPLE 1

This is an example in which the mixture of CEVE and CE was produced by a decomposition reaction of CEE.

A 300 cm glass flask was fitted with a packed column having 43 cm length, and an inlet at the point 4 cm under the lower end of the packing in the column.

After 150 g of CEE were charged to the flask, the flask was heated and the inner pressure was gradually decreased. When the flask was filled with the vapor of CEE, the CEE containing 0.2% of phosphoric acid was introduced continuously to the flask so as to keep the liquid amount constant in the flask.

After the decomposition of CEE began, the pressure was kept at 100 mmHg, and, at the same time, a solution consisting of about 65 weight parts of CEVE, about 3 parts of CE and 32 parts of triethyl amine was introduced from the inlet by a velo-city of about 2 g/Hr of triethyl amine.

When 200 g of the phosphoric acid solution was introduced, the introduction was stopped and the decomposition was continued till the weight of the residue was shown to be about 7 g. Then, the reaction was stopped.

The weight of the distillate was 405 g, which clonsisted of 53.8% of CEVE, 41.8% of CE, 2.2% of triethyl amine, 0.9% of CEE and 2.0% of others, which suggested the decomposition proceeded nearly quantatively.

EXAMPLE 1

The distillate mentioned above was distilled again and 121 g of the azeotropic fraction consisting of 89% of CEVE, 7.3% of CE, 3.4% of triethyl amine and 0.3% of others were obtained.

On the other hand, the mixture staying in the distillation still consisted of 1.2% of CEVE, 93.5% of CE, 0.1% of triethyl amine and 2.6% of others. (This can be clearly recycled to the production of CEE and is called as Fraction A.)

Next, the triethyl amine fraction (This fraction consists of 32.5% of triethyl amine, 65.1% of CEVE and 2.4% of CE, and is called as Fraction B.) was distilled out from the above azeotropic fraction, then, to 105.6 g of the residual part mainly consisting of CEVE (91.7% of CEVE, 7.8% of CE and 0.3% of others), 0.05% of phosphoric acid to the residual part was added. And the mixture was stirred for 110 minutes at the ambient temperature.

As a result, the reaction mixture containing 80.5% of CEVE, 18.6% of CEE, 0.2% of CE and 0.7% of others was obtained, which showed almost all of CE was changed to CEE.

At last, by the rectification of the above mixture under the reduced pressure of 65 mmHg at the temperature below 75° C., 77 g of the product werr obtained. It consisted of 99.2% of CEVE, less than 0.1% of CE and about 0.8% of others, and the water content was 7 ppm.

On the other hand, the residual part of this rectification had the composition of 21.4% of CEVE, 0.8% of CE and 77.2% of CEE. Other by-products had been scarcely produced. (This part is called as Fraction C.)

The recovery rate of the produced CEVE was 98%, that of the by-produced CE was 99% and that of the employed triethyl amine was 96%.

REFERENCE EXAMPLE 2

Reference Example 1 was repeated by using Fraction C as a portion of the CEE containing phosphoric acid, and using Fraction B as a portion of the solution consisting of CEVE, triethyl amine and others. Total amount of the distillate was 402 g, and its composition was almost same as that of Reference Example 1. (53.6% of CEVE, 41.6% of CE, 2.4% of triethyl amine and 2.4% of others)

EXAMPLE 2

Both of the azeotropic distillation and the distillation for separating the triethyl amine fraction were repeated, and 107.8 g of the residual part consisting of 90.8% of CEVE, 8.3% of CE and 0.5% of others were obtained from 200 g of the distillate mentioned in Reference Example 2.

Then, all of the residual part was reacted with 0.05% of concentrated hydrochloric acid for 10 minutes at 85° C. This reaction mixture was rectified under a similar condition mentioned in Example 1, and 82 g of the product were obtained. It consisted of 99.3% of CEVE, less than 0.1% of CE and about 0.6% of others, and the water content was 5 ppm.

The recovery rate of the produced CEVE was 99%, those of the by-produced CE and the triethyl amine were 99% and 98% respectively.

EXAMPLE 3

By distillation and the separation of triethyl amine fraction, 110 g of the residual part consisting of 91.8% of CEVE, 7.9% of CE and 0.1% of others were obtained from 200 g of the decomposition liquid consisting of 54.8% of CEVE, 42.0% of CE, 1.9% of triethyl amine, 0.8% of CEE and 0.5% of others.

All of the above residual part was reacted with 0.1% of p-toluene sulofonic acid for 10 minutes at 90° C.

The reaction mixture was rectified under a similar condition as was mentioned in Example 1, and 86 g of the product consisting of 99.4% of CEVE, less than 0.1% of CE and about 0.5% of others were obtained. It contained only 6 ppm of water.

The recovery rate of CEVE was 98.5%, and those of CE and triethyl amine were 99% and 95% respectively.

COMPARISON EXAMPLE 1

By the process disclosed in example 1 of U.S. Pat. No. 3,023,250, 200 g of thermal decomposition product were obtained. Then, this product was distilled, and 122 g of the azeotropic fraction consisting of 88.5% of CEVE, 7.3% of CE, 3.6% of triethyl amine and 0.6% of others were obtained.

After carbon dioxide gas was introduced continuously for 1 hour into this fraction, the fraction was washed with almost same amount of water to the fraction, and 102 g of the organic layer were separated. The part of organic compounds in this layer consisted of 96.9% of CEVE, 2.6% of CE and 0.5% of others.

This layer was distilled, 6 g of the initial fraction were separated to remove water, and the crude product consisting of 96.6% of CEVE, 2.8% of CE and 0.6% of others was obtained. But the crude product contained 210 ppm of water still more and could not be dried only by distillation.

Washing with an equal amount of water for three times and another distillation were necessary for decreasing the content of CE. And, at last, 90 g of purified CEVE were obtained.

Even if the recycle uses of the above initial fraction and each distillation residue were considered, the recovery rate of CEVE was 84%, and that of CE was 87%. Further, the triethyl amine employed could not be recovered, and about three times more amount of waste water containing CE and triethyl amine carbonate salt remained.

What we claim is:

1. An isolation process of 2-chloroethyl vinyl ether having a high purity from the thermal decomposition mixture of 1,1-di(2-chloroethoxy)ethane, which comprises the following procedures:
   (1) separating the fraction consisting mainly of 2-chloroethyl vinyl ether and partially of 2-chloroethanol from the said thermal decomposition mixture;
   (2) acidifying the said fraction, then without separating the above two compounds, reacting the said 2-chloroethanol with a part of the 2-chloroethyl vinyl ether at a temperature below 100° C. to 1,1-di(2-chloroethoxy)ethane, and making the said fraction consist of 2-chloroethyl vinyl ether and 1,1-di(2-chloroethoxy)ethane;
   (3) isolating 2-chloroethyl vinyl ether from 1,1-di(2-chloroethoxy)ethane by rectification.

* * * * *